(12) United States Patent
Kang (10) Patent No.: US 12,394,529 B2
(45) Date of Patent: Aug. 19, 2025

(54) APPARATUS AND METHOD FOR ESTIMATING PERSONALIZED PROBABILITY OF DRUG SIDE EFFECTS

(71) Applicant: CHUNGBUK NATIONAL UNIVERSITY HOSPITAL, Cheongju-si (KR)

(72) Inventor: Min Gyu Kang, Cheongju-si (KR)

(73) Assignee: CHUNGBUK NATIONAL UNIVERSITY HOSPITAL, Cheongju-si (KR)

( * ) Notice: Subject to any disclaimer, the term of this patent is extended or adjusted under 35 U.S.C. 154(b) by 98 days.

(21) Appl. No.: 18/345,630

(22) Filed: Jun. 30, 2023

(65) Prior Publication Data
US 2024/0013930 A1    Jan. 11, 2024

Related U.S. Application Data

(63) Continuation of application No. PCT/KR2021/020126, filed on Dec. 29, 2021.

(30) Foreign Application Priority Data

Dec. 30, 2020    (KR) .................. 10-2020-0187377

(51) Int. Cl.
*G16H 70/40*    (2018.01)
(52) U.S. Cl.
CPC .................. *G16H 70/40* (2018.01)
(58) Field of Classification Search
CPC ........ G16H 70/40; G16H 20/10; G16H 10/60; G16H 50/30; G16H 80/00
See application file for complete search history.

(56) References Cited

U.S. PATENT DOCUMENTS

| | | | |
|---|---|---|---|
| 2007/0219825 A1* | 9/2007 | Maetzold | G16H 20/10 707/999.102 |
| 2010/0235378 A1* | 9/2010 | Armstrong | G06Q 10/10 707/769 |

(Continued)

FOREIGN PATENT DOCUMENTS

| | | |
|---|---|---|
| JP | 5365042 B2 | 12/2013 |
| JP | 2018-147463 A | 9/2018 |

(Continued)

OTHER PUBLICATIONS

R. Majethia, V. Mishra, A. Singhal, Lakshmi Manasa K, K. Sahiti and V. Nandwani, "PeopleSave: Recommending effective drugs through web crowdsourcing," 2016 8th International Conference on Communication Systems and Networks (COMSNETS), Bangalore, India, 2016, pp. 1-6, doi: 10.1109/COMSNETS.2016.7440000 (Year: 2016).*

(Continued)

*Primary Examiner* — Sun M Li
(74) *Attorney, Agent, or Firm* — Studebaker Brackett PLLC (57) ABSTRACT

A method for estimating personalized probability of a drug side effect includes identifying a drug taken by a subject, identifying an experience of a side effect, which is produced as the subject takes the drug, and input by the subject, and estimating a probability of the side effect of the subject in (Continued)

relation to the drug, based on the experience of the side effect of the subject, which are executed by a computing device.

8 Claims, 11 Drawing Sheets

(56) References Cited

U.S. PATENT DOCUMENTS

| | | | |
|---|---|---|---|
| 2012/0041778 A1* | 2/2012 | Kraft | A61J 3/074 215/250 |
| 2013/0046554 A1* | 2/2013 | Williams | G16H 10/60 705/2 |
| 2013/0268288 A1* | 10/2013 | Fujimaki | G06Q 10/10 705/2 |
| 2014/0066844 A1* | 3/2014 | Rule | A61B 5/1427 604/66 |
| 2015/0220687 A1* | 8/2015 | An | G16H 70/40 707/731 |
| 2019/0043610 A1* | 2/2019 | Vaughan | A61B 5/4088 |
| 2020/0321096 A1* | 10/2020 | Mould | G16H 50/20 |
| 2021/0043293 A1* | 2/2021 | Valuck | G06N 20/20 |
| 2024/0079109 A1* | 3/2024 | Bilbault | G16H 70/40 |

FOREIGN PATENT DOCUMENTS

| | | |
|---|---|---|
| KR | 10-2008-0042256 A | 5/2008 |
| KR | 10-2009-0071564 A | 7/2009 |
| KR | 10-2014-0048673 A | 4/2014 |
| KR | 10-2019-0054762 A | 5/2019 |
| KR | 10-2020-0136950 A | 12/2020 |

OTHER PUBLICATIONS

A. K. Tripathy, N. Joshi, H. Kale, M. Durando and L. Carvalho, "Detection of adverse drug events through data mining techniques," 2015 International Conference on Technologies for Sustainable Development (ICTSD), Mumbai, India, 2015, pp. 1-6, doi: 10.1109/ICTSD.2015.7095897. (Year: 2015).*

Majumder S, Deen MJ. Smartphone Sensors for Health Monitoring and Diagnosis. Sensors (Basel). May 9, 2019;19(9):2164. doi: 10.3390/s19092164. PMID: 31075985; PMCID: PMC6539461. (Year: 2019).*

Lester CA, Li J, Ding Y, Rowell B, Yang J', Kontar RA. Performance evaluation of a prescription medication image classification model: an observational cohort. NPJ Digit Med. Jul. 27, 2021;4(1):118. doi: 10.1038/s41746-021-00483-8.. doi: 10.1038/s41746-022-000564-2.PMID: 34315995; PMCID: PM08316316. (Year: 2021).*

R. Majethia, V. Mishra, A. Singhal, Lakshmi Manasa K, K. Sahiti and V. Nandwani, "PeopleSave: Recommending effective drugs through web crowdsourcing," 2016 8th Intl Conf on Communication Systems and Networks (COMSNETS), Bangalore, India, 2016, pp. 1-6, doi: 10.1109/COMSNETS.2016.7440000 (Year 2016) (Year: 2016).*

An Office Action mailed by the Korean Intellectual Property Office on May 30, 2023, which corresponds to Korean Patent Application 10-2020-0187377; with English language translation.

International Search Report issued in PCT/KR2021/020126; mailed Apr. 8, 2022.

Written Opinion of the International Searching Authority issued in PCT/KR2021/020126; mailed Apr. 8, 2022.

* cited by examiner

| "a" drug | First symptom | Second symptom |
|---|---|---|
| "A" ingredient | 10% | 5% |
| "B" ingredient | 20% | |

FIG. 7A

| Patient | Drug taken | First symptom | Second symptom |
|---|---|---|---|
| Patient of 'TOM' | "a" drug (first) | Present | Present |

FIG. 7B

| Patient | Drug taken | First symptom | Second symptom |
|---|---|---|---|
| Patient of 'TOM' | "a" drug (Twice) | Present | Absent |

FIG. 8A

| "b" drug | First symptom | Second symptom |
|---|---|---|
| "A" ingredient | 10% | 50% |
| "C" ingredient | 20% | |

FIG. 8B

| Patient | Drug taken | First symptom | Second symptom |
|---|---|---|---|
| Patient of 'TOM' | "b" drug (first) | Present | Absent |

FIG. 9

APPARATUS AND METHOD FOR ESTIMATING PERSONALIZED PROBABILITY OF DRUG SIDE EFFECTS

CROSS-REFERENCE TO RELATED APPLICATIONS

The present application is a continuation of International Patent Application No. PCT/KR2021/020126, filed on Dec. 29, 2021, which is based upon and claims the benefit of priority to Korean Patent Application No. 10-2020-0187377 filed on Dec. 30, 2020. The disclosures of the above-listed applications are hereby incorporated by reference herein in their entirety.

BACKGROUND

Embodiments of the inventive concept described herein relate to an apparatus and a method for estimating personalized probability of a drug side effect, and more particularly, an apparatus and a method for estimating the probability of a drug side effect, based on an individual experience made in taking a drug.

Individuals are taking drugs prescribed from hospitals or taking various medications depending on the determination of individuals or the advice of pharmacists.

Although the drugs have the potential to cause a mediated user to have various side effects, the potential is merely a statistical probability before individuals take the drugs, and the individuals actually experience side effects with mutually different possibilities. The probability in which a medicated user experiences the side effect when taking a drug at a specific time point, may be varied depending on individual characteristics, based on side effects previously experienced, when the medicated user have an experience of taking the drug several times.

In other words, among mutually different individuals taking the same drug having the same statistical side effect probability, any individual may experience a relevant side effect, but another individual may not experience the relevant side effect. Even though the drug has a higher statistical side effect probability for a specific ingredient, the specific individual may have a physical body that does not show the relevant side effect of the drug.

However, when an individual takes a drug containing multiple chemicals or multiple medications for a disease, it is difficult to detect a drug of the side effect suffered by each individual or to detect ingredients of a drug of the side effect suffered by the individual. Accordingly, it is difficult for the individual to avoid the drug or the ingredient producing the side effect, to prevent the experience of the side effect.

When receiving a prescription at a hospital, an individual lets a doctor know the side effects experienced by the individual, and the doctor may exclude a drug having a possibility of the side effect from the prescription. However, it is difficult to apply the exclusion to all drugs to be taken by the individual.

Although there is a conventional technology of excluding a drug producing a side effect experienced by an individual from a prescription, it is difficult for the individual having various drugs to detect the drug producing the side effect. Especially, it is difficult to apply the technology when the individual takes a drug out of the prescription.

Recently, there have been attempts to estimate the possibility of a drug side effect, based on an individual gene or based on individual physiological characteristics. However, the attempts have not yet been recognized as official personalized side effect probability technologies, and the individual access to the attempts is economically and methodically difficult.

Therefore, there is a need for a technology which allows an individual to easily detect a drug which is likely to have a side effect on the individual, even if the technology has no accurate probability corresponding to the gold standard.

SUMMARY

Embodiments of the inventive concept provide an apparatus and a method for estimating personalized probability of drug side effects, based on an experience in which an individual takes a drug.

Embodiments of the inventive concept provide an apparatus and a method for estimating personalized probability of drug side effects, based on whether a side effect is produced or not when the individual takes the drug.

Embodiments of the inventive concept provide an apparatus and a method for estimating personalized probability of drug side effects, based on the strength of a side effect produced as an individual takes a drug and a time in which the individual previously takes the drug.

An object to be achieved by the inventive concept is not limited to the above-mentioned objects, and other objects and advantages of the inventive concept which are not mentioned will be understood by the following description and will be more clearly understood by the embodiment of the inventive concept. In addition, it may be seen that the challenges and advantages to be solved by the inventive concept may be realized by means indicated in the scope of patent claims and combinations thereof.

According to an embodiment, a method for estimating personalized probability of a drug side effect includes identifying a drug taken by a subject, identifying an experience of a side effect, which is produced as the subject takes the drug, and input by the subject, and estimating a probability of the side effect of the subject in relation to the drug, based on the experience of the side effect of the subject, which are executed by a computing device.

According to an embodiment, a computing device may include a processor, and a memory operatively connected to the processor to store at least one code executed by the processor. The memory may store codes that when executed by the processor, cause the processor to: identify a drug taken by a subject; identify a side effect input from the subject, as the subject takes the drug; and estimate a probability of the side effect of the subject, in relation to the drug, based on an experience of the side effect of the subject.

According to an embodiment of the inventive concept, in the apparatus and method for estimating personalized probability of drug side effects, the individual may easily detect the drug and the drug ingredient producing the side effect to be caused to the individual with the higher probability.

According to an embodiment of the inventive concept, in the apparatus and method for estimating personalized probability of drug side effects, the individual may exclude the side effects to be caused by the drug personally taken, such that the secondary damage caused by the side effects may be prevented.

According to an embodiment of the inventive concept, in the apparatus and method for estimating personalized probability of drug side effects, the individual may easily detect the drug and the drug ingredient, which have side effects to be caused to the individual with the higher probability, of the various drugs taken by the individual.

Problems to be solved by the inventive concept are not limited to the problems mentioned above, and other problems not mentioned will be clearly understood by those skilled in the art from the following description.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, embodiments disclosed in the inventive concept will be described with reference to accompanying drawings, same or similar components will be assigned with same reference numerals, and the redundant repeat thereof will be omitted. Suffixes of components, such as "module" and "unit", which are employed in the following description, are merely intended to facilitate description of the specification, and the suffix itself is not intended to give any special meaning or function. In addition, in the following description of the inventive concept, a detailed description of well-known art or functions will be ruled out in order not to unnecessarily obscure the gist of the inventive concept. In addition, the accompanying drawings are provided to allow those skilled in the art to easily understand an embodiment of the inventive concept, and the technical spirit of the inventive concept is not limited thereto accompanying drawings. The inventive concept is to cover all modifications, equivalents, and alternatives falling within the spirit and scope of the inventive concept.

Although the terms including ordinal numbers, such as "first" and "second" may be used to describe various components, the components are not limited to the terms. The terms are used only to differentiate one component from another component.

It will be understood that when a component is referred to as being "coupled with/to" or "connected to" another component, the component may be directly coupled with/to or connected to the another component or an intervening component may be present therebetween. In contrast, when an element is referred to as being "directly connected" or "directly coupled" to another element, there are no intervening elements.

Figure 1:
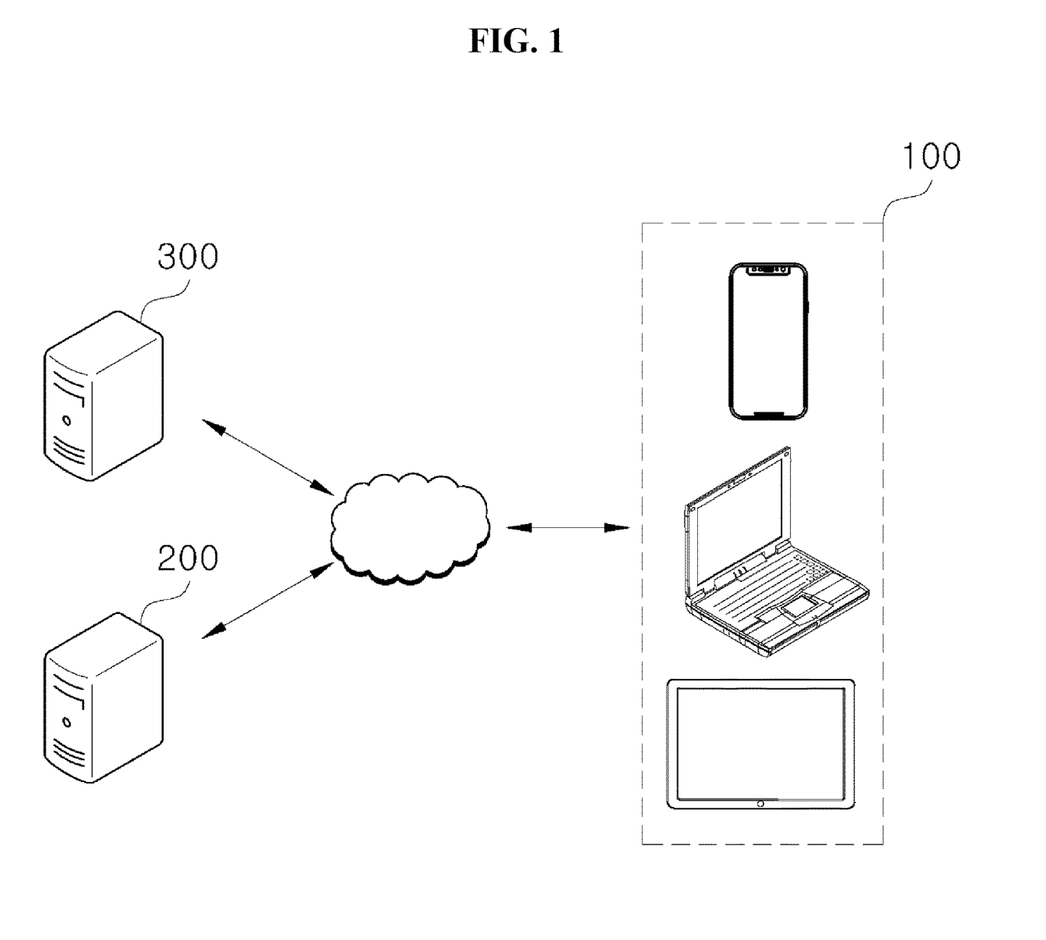
FIG. 1 is a view illustrating an environment in which an apparatus and method for estimating personalized probability of drug side effects are realized, based on a drug experience of an individual, according to an embodiment of the inventive concept.

The following description will be made with reference to FIG. 1 regarding an environment in which the apparatus and method for estimating personalized probability of drug side effects are realized, according to an embodiment of the inventive concept.

In the present specification, the expression of a drug, chemicals, or a medicine may be a drug composed of a single ingredient or a composite ingredient and do not have mutual different meanings.

In this specification, taking is a concept including the case in which a drug is administrated into a body in various forms, such as an oral use, taking through an injection, taking through a patch, skin application of ointments, and injection through nasal or eye mucous membranes.

The apparatus and method for estimating personalized probability of the drug side effects according to an embodiment of the inventive concept may be realized using a user terminal or a server device. Although the following description has been made in that the apparatus and method for estimating personalized probability of drug side effects are realized in the server device, the apparatus and method for estimating personalized probability of drug side effects may be realized in the user terminal.

The environment for realizing the apparatus and method for estimating personalized probability of drug side effects according to an embodiment of the inventive concept may include a user terminal 100 and a server device 200. When a database including statistical information on a drug side effect is realized in the form of a separate device, a drug side effect database device 300 may be included.

A person who has taken the drug may input, through the user terminal 100, information on a drug taken by the person, on whether a side effect is produced after the drug is taken, and the type of the relevant side effect when the side effect is produced.

Figure 9:
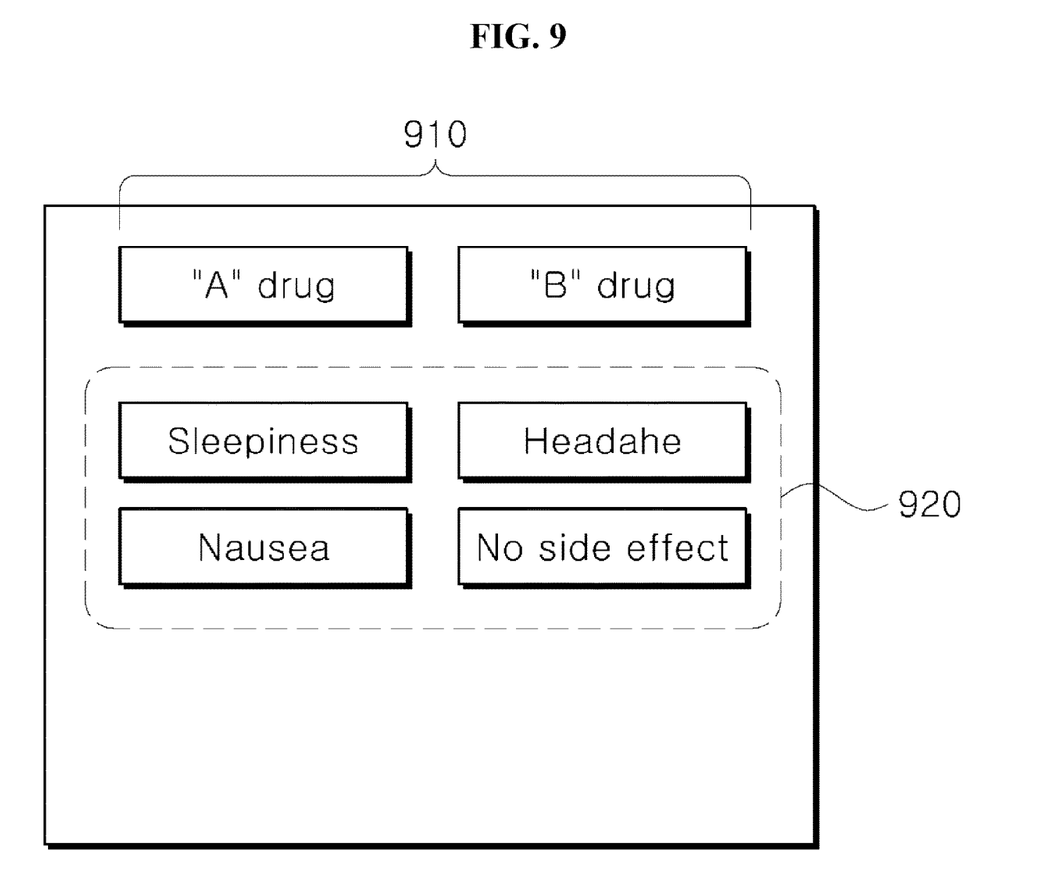
FIG. 9 is a block diagram illustrating the interface of a user terminal, according to an embodiment of the inventive concept.

Referring to FIG. 9, when a user inputs a drug 910 taken into the user terminal 100, the server device 200 may acquire an ingredient contained in the drug or side effects 920 related to the drug from the drug side effect database 300 and provide the drug to the user terminal 100. The user may select a side effect, which is experienced by the user, of the side effects received from the server device 200 or select that the side effects are not produced. The server device 200 updates the side effect probability of the user with respect to the drug taken by the user or an ingredient contained in the drug.

The server device 200 acquires the statistical side effect probability of a drug taken by the user or of an ingredient contained in the drug from the drug side effect database 300 or a database provided therein, sets the statistical side effect probability as an initial personalized drug side effect probability for the drug taken by the user or the ingredient contained in the drug, and re-selects (updates) the personalized probability of the drug side effect with respect to each experience in which the user takes the drug. The server device 200 reflects this even when the user does not experience the side effect such that the personalized probability of the drug side effect is re-selected.

The server device 200 may receive a specific drug or a specific ingredient from the user terminal 100 and may provide the personalized drug side effect probability for the specific drug or the specific ingredient.

When the side effect probability of an individual for the specific drug exceeds a preset threshold value or when the number of times of side effects exceeds a preset number of times, that is, a preset reference, the server device 200 may provide, to the user terminal 100, that the side effect probability of the individual for the specific drug exceeds the preset threshold value or that the number of times of side effects exceeds the preset number of times.

The user terminal 100 may receive the personalized drug side effect probability for the specific drug or the specific ingredient from the server device 200, and the user may identify this when the user purchases the specific drug. Alternatively, when prescribing, dispensing, or selling drugs to a specific patient, a pharmacy or hospital terminal may receive a personalized drug side effect probability for the specific drug or ingredient of the specific patient, such that a drug having the higher side effect probability is excluded from drugs provided to the relevant patient.

Figure 2:
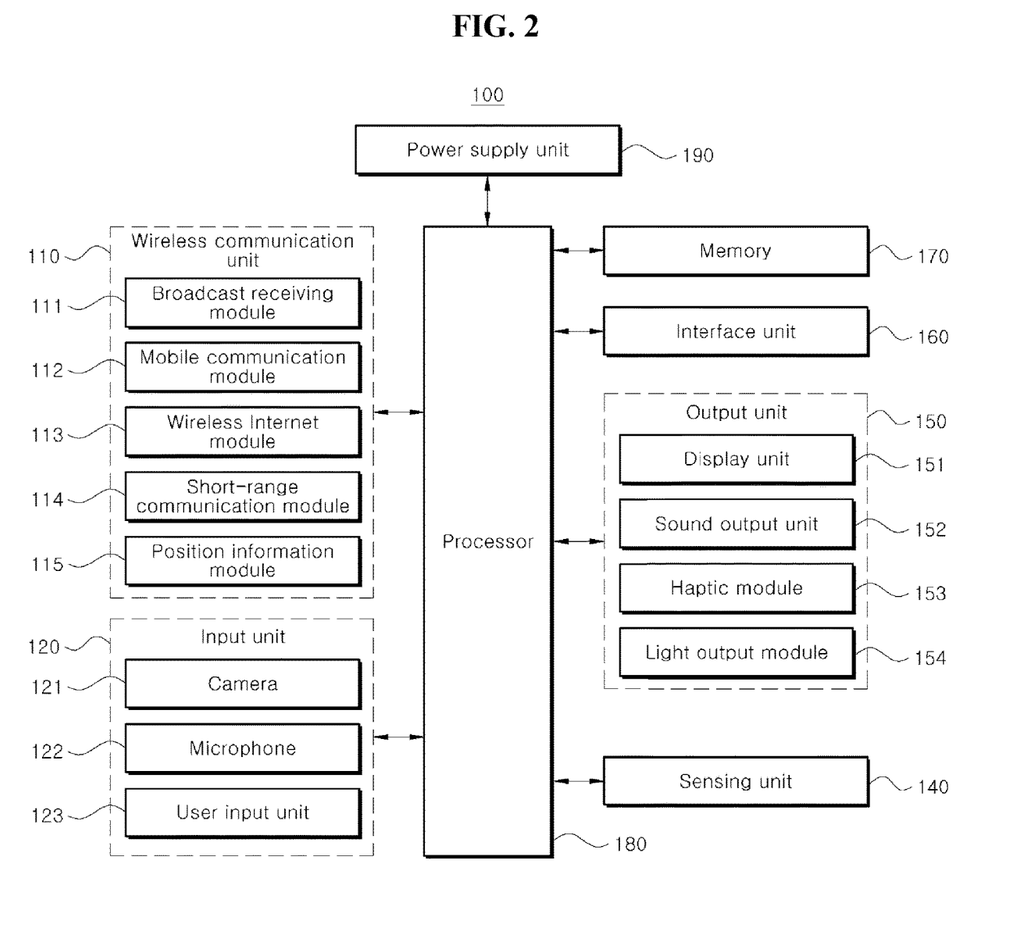
FIG. 2 is a block diagram illustrating the configuration of a user terminal, according to an embodiment of the inventive concept.

Hereinafter, the configuration of the user terminal 100 will be described with reference to FIG. 2.

The user terminal 100 may include a communication interface to make communication with the server device 200.

The communication interface may include a wireless communication unit or a wired communication unit.

The wireless communication unit may include at least one of a mobile communication module, a wireless Internet module, a short-range communication module, and a position information module.

The mobile communication module transmits or receives a wireless signal together with at least one of a base station, an external terminal or server over a mobile communication network constructed based on technical standards or communication schemes (for example, Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), or Long Term Evolution (LTE), Long Term Evolution (LTE-A)-Advanced).

The wireless Internet module, which refers to a module for wireless Internet access, may be embedded in or provided out of the user terminal 100. The wireless Internet module is configured to transmit and receive wireless signals in a communication network according to wireless Internet technologies.

The wireless communication technology may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), or Long Term Evolution-Advanced (LTE-A).

The short-range communication module, which is used for short range communication, may support a short-range communication by using at least one of Bluetooth™, Radio Frequency Identification Bluetooth (RFID), Infrared Data Association (IrDA), Ultra Wideband (UWB), ZigBee, Near Field Communication (NFC), Wireless-Fidelity (Wi-Fi), Wi-Fi Direct, and Wireless Universal Serial Bus (USB) technologies.

The position information module, which is a module to acquire the position (or the current position) of the user terminal 100, may representatively include a global positioning system (GPS) module or a wireless fidelity (WiFi) module. For example, the terminal may acquire the position of the user terminal 100, by using a signal received from a GPS satellite, when the GPS module is utilized.

According to an embodiment, the user terminal 100 may include an input unit to receive the type of a drug taken by a user or the type of a side effect of the user.

The input unit may include a micro-phone to receive an audio signal and a user input unit to receive information from the user.

The user input unit may include a mechanical input unit (or a mechanical key, a mechanical button, a dome switch, a jog wheel, or a jog switch), and a touch-type input unit. For example, the touch input unit may include a virtual key, a soft key, or a visual key displayed on a touchscreen through software processing or may include a touch key disposed in a portion other than the touch screen.

According to an embodiment, the user terminal 100 may include an output unit to transmit information to the user.

The output unit, which is to generate an output associated with a visual, auditory, or tactile sensation, may include at least one of a display unit, a sound output unit, or a light output unit.

The display unit displays (outputs) information processed by the user terminal 100. For example, the display unit may display the type of side effects of the drug or the ingredients contained in the drug, which is provided by the server device 200 in relation to the drug taken by the user.

The sound output unit may include at least one of a receiver, a speaker, and a buzzer.

The user terminal 100 may include an interface unit which serves as a passage with various types of external devices connected to the user terminal 100. The interface unit may include at least one of a wired/wireless data port, a memory card port, a port connecting a device equipped with an identification module, an audio I/O (Input/Output) port, a video I/O (Input/Output) port, and an earphone port.

Figure 3:
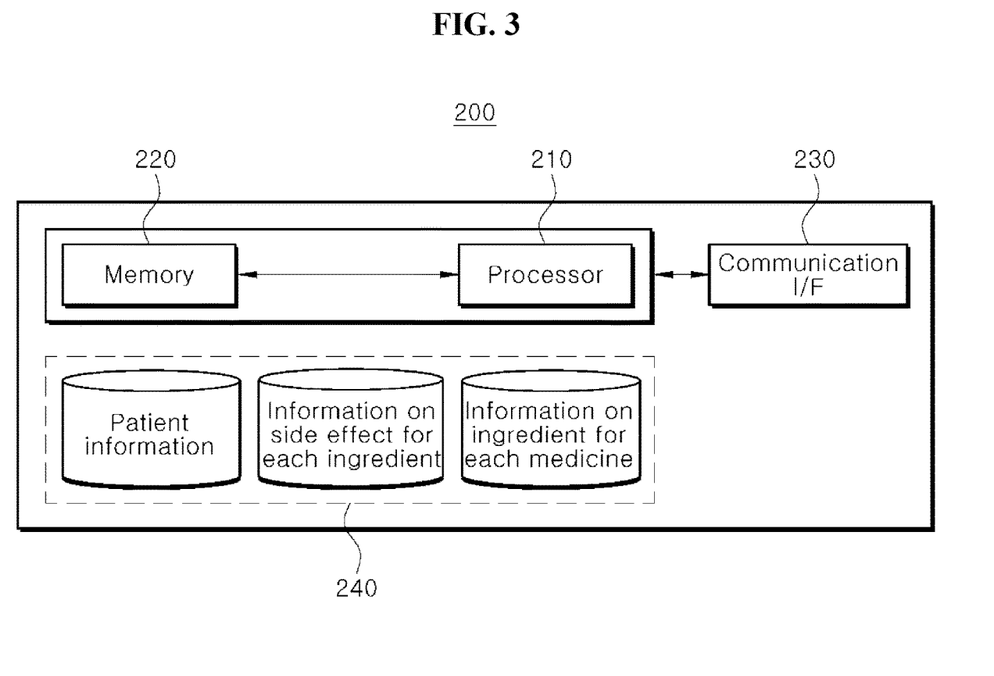
FIG. 3 is a block diagram illustrating the configuration of a server device, according to an embodiment of the inventive concept.

The configuration of the server device 200 according to an embodiment of the inventive concept will be described with reference to FIG. 3.

The server device 200 may store information on a physical body of a subject, a diagnosis name (which may be a diagnosis code) in prescribing the drug of the subject, the type of drug taken, the type of an ingredient contained in the drug, information on the dose and the time taken when the drug is taken, whether a side effect experienced when the drug is taken is produced, or the type of the side effect.

The server device 200 may store information on a drug, statistical information of a side effect of an ingredient of the drug, or information on the ingredient of the drug.

The server device 200 may store medical treatment information, prescription information, or body information including a diagnosis disease name (which may be a diagnosis code) of a patient.

The information stored by the server device 200 may be implemented (store) in an external separate database or a storage device 240 which is a part of the server device 200.

A processor 210 of the server device 200 may estimate the personalized drug side effect probability of a user by using information on the ingredient of the drug and statistical information of the drug or ingredients contained in the drug, based on the type of the drug taken by the user, whether the side effect is produced, and the type of the side effect, which are received through a communication interface 230, from the user terminal 100.

The processor 210 of the server device 200 may estimate the personalized drug side effect probability of the user, based on whether the side effect is not produced, as well as whether the side effect is produced, after the user takes the drug. In this case, mutually different algorithms may be applied to estimating the personalized drug side effect probability of the user.

The algorithm of estimating the personalized drug side effect probability of the user may be implemented in hardware, software, or the combination of hardware and software. When a portion or the entire portion of the algorithm is implemented in software, at least one instruction constituting the algorithm may be stored in a memory 220.

Figure 4:
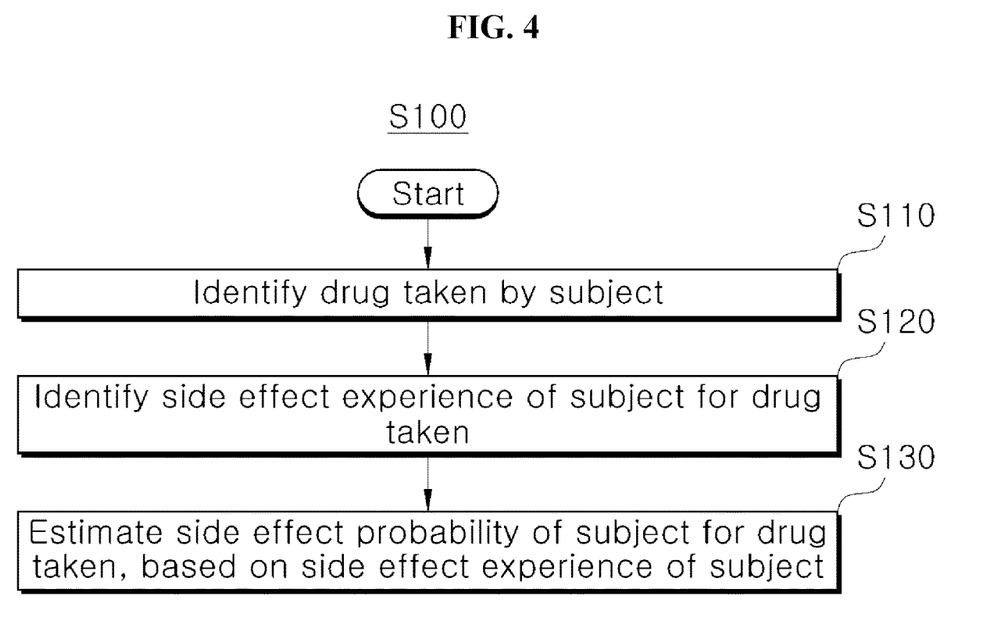
FIG. 4 is a flowchart illustrating a method for estimating the probability of a drug side effect, according to an embodiment of the inventive concept.

Hereinafter, the method for estimating personalized probability of drug side effects according to an embodiment of the inventive concept will be described with reference to FIG. 4.

The method for estimating personalized probability of drug side effects may be implemented even in the user terminal. However, the following description will be made on the assumption that the method for estimating personalized probability of drug side effects is implemented in the server device.

The server device 200 identifies a drug taken by the user, which is input by the user through the user terminal 100 (S110). The drug taken by the user may be a drug including a single ingredient or a drug including composite ingredients, or multiple drugs taken at the same time or in a specific period. The drug may have a product name, which is recognized through a camera device of the user terminal 100, on a product package, a product name recognized through a code, such as a QR code, of the product package, or a product name input through the input of the user. In addition, the server device 200 may identify the diagnostic name or diagnostic code printed on the prescription in a similar way or access a separate medical information system (OCS, HIS, EMR, etc.) to identify the diagnostic name or diagnostic code.

The server device 200 may identify whether the side effect of the user is produced as the user takes the drug, or may identify the experience of the side effect, which includes the type of the side effect (S120).

Figure 6:
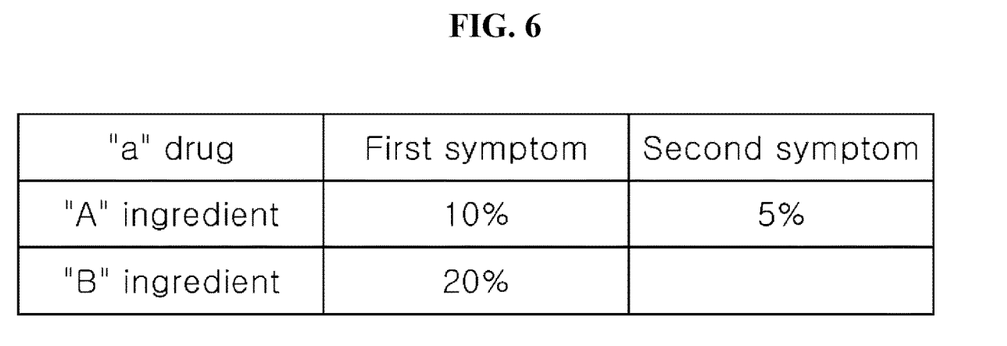
FIG. 6 is a view illustrating information on a drug side effect information in a side-effect database, according to an embodiment of the inventive concept.

The server device 200 estimates the side effect probability of the user for the individual drug taken based on the side effect experience of the user (S130). When the user takes the relevant drug at the initial stage, the server device 200 acquires the statistical side effect probability, as illustrated in FIG. 6, of the relevant drug or the ingredient of the drug from the database, sets the acquired probability as a basic side effect probability of the user for the relevant drug, and estimates a drug side effect probability based on the side effect experience of the user, which is identified.

The side effect experience includes that the side effect is not produced, and the server device 200 estimates the drug side effect probability based on the side effect experience of the user by reflecting the experience, in which the side effect is not produced, after the user takes the specific drug. Accordingly, whenever receiving an experience in which the user takes the same drug, or an experience in which the user takes a drug containing the same ingredient, the server device 200 updates the drug side effect probability of the user with respect to the relevant drug or the ingredient included in the drug, with respect to all experiences in which the side effect is produced or not after the drug is taken.

The server device 200 estimates the drug side effect probability of the user for the drug by applying mutually different algorithms to an experience in which the side effect is produced or an experience in which the side effect is not produced, after the user takes the drug, and the details thereof will be described later.

Figure 5:
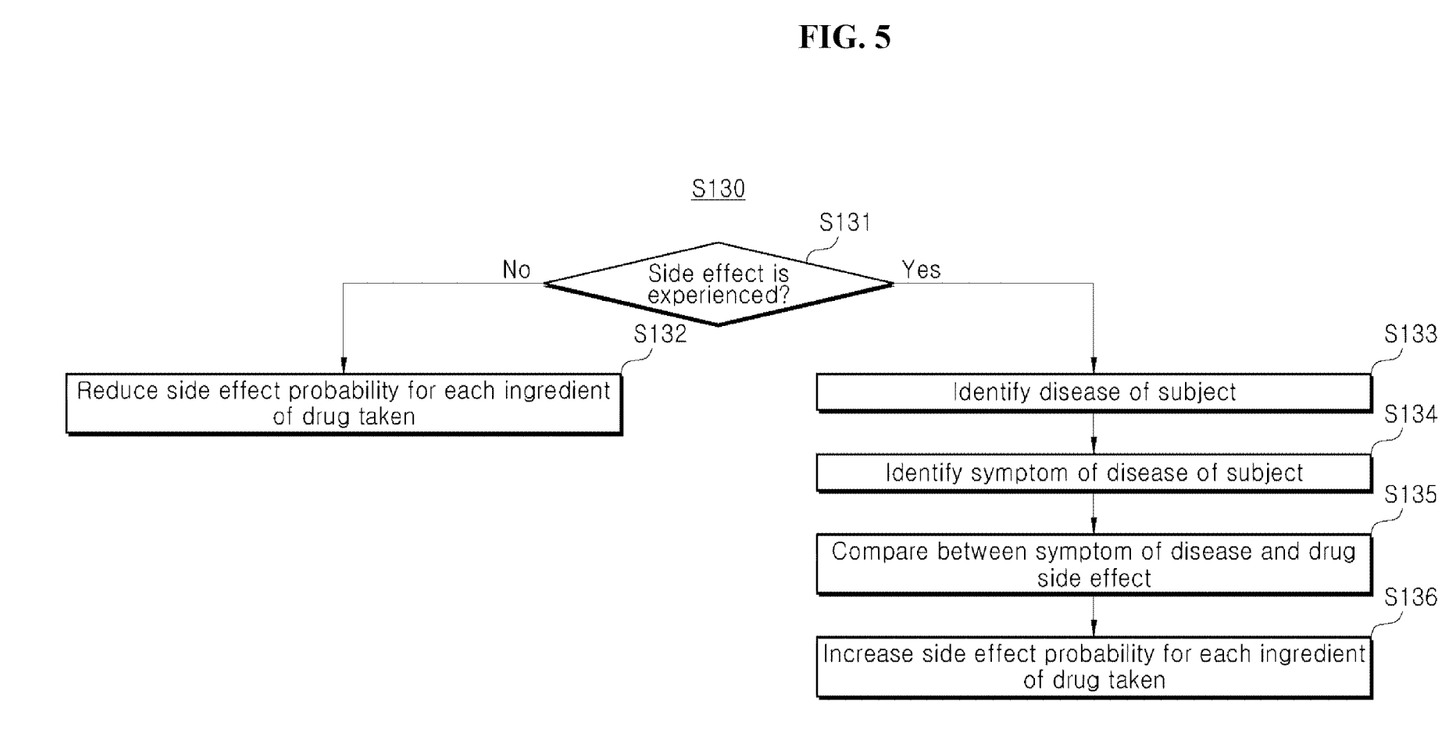
FIG. 5 is a flowchart illustrating a method for estimating the probability of a drug side effect, according to an embodiment of the inventive concept.

Hereinafter, the detailed method (S130) for estimating personalized probability of drug side effects according to an embodiment of the inventive concept will be described with reference to FIG. 5.

The server device 200 may estimate the drug side effect probability of the user for the drug by applying mutually different algorithms to an experience in which the side effect is produced or an experience in which the side effect is not produced, after the user takes the drug, and may reduce the drug side effect probability of the user with respect to the drug taken or the ingredient of the drug, when the side effect is not produced (S132).

In this case, the server device 200 may reduce the increment or the decrement of the drug side effect probability of the user with respect to ingredients when the user takes a drug or multiple drugs including complex ingredients. According to an embodiment, when the user takes multiple drugs, an algorithm of increasing or decreasing a specific side effect probability is to uniformly increase or decrease the specific side effect probability by dividing the side effect probability by the number of drugs taken or is to apply a weight to a previous side effect probability and to reflect the result.

When the specific drug is taken by a user and the side effect is not produced at the initial stage, the server device 200 acquires the statistical side effect probability as illustrated in FIG. 6 and sets the statistical side effect probability as the basic side effect probability of the user for the relevant drug. For example, referring to FIG. 6, the statistical side effect probability for a first symptom of an 'A' ingredient is 10%, and the statistical side effect probability for a second symptom of the 'A' ingredient is 5%. Thereafter, the server device 200 may multiply the basic side effect probability by a preset disincentive constant of reflecting the experience of the user, in which the side effect is not produced. In this case, the disincentive constant may be less than '1' and may be experimentally determined.

For example, when the disincentive constant is 0.5, and when the side effect is not produced after the user takes a drug including the 'A' ingredient and the 'B' ingredient at the first stage, the server device 200 may estimate the side effect probability of the first symptom of the user for the 'A' ingredient as being 5% (=10%×0.5), may estimate the side effect probability of the second symptom of the user for the 'A' ingredient as being 2.5%(=5%×0.5), and may estimate the side effect probability of the first symptom of the user for the 'B' ingredient as being 10% (=20%×0.5)

Thereafter, when the side effect is not produced again after the user takes the same drug, the server device 200 may re-estimate (update) the side effect probability of the user for each symptom for the 'A' and 'B' ingredients by using the disincentive constant and based on the side effect probability of the user, which is previously estimated.

The method for estimating the side effect probability of the user will be described with reference to FIGS. 5 and 7A when the side effect is produced.

Figure 7A:
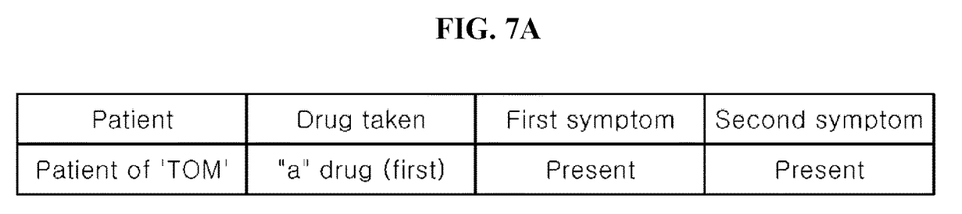
FIGS. 7A-7B and FIGS. 8A-8B are views illustrating individual side-effect experience to describe the method for estimating personalized probability of a drug side effect, according to an embodiment of the inventive concept.

When a user as illustrated in FIG. 7A takes a specific drug including the 'A' and 'B' ingredients at the first stage, and the side effect is produced, the server device 200 may identify the disease of the user (S133). The server device 200 may identify prescription information having a disease code of a patient, which is recorded therein, from an electronic medical record (EMR) server or may identify the prescription information through the input of the user. The EMR server is a concept which includes not only a medical record management server managed by a public institution, but also a medical record management or delivery server managed by a private institution to share or deliver a medical record of each hospital. As described above, the user may recognize, from a prescription, the disease code printed on the prescription through the camera device of the user terminal 100 as described above, and may directly input the disease code.

The server device 200 may identify the symptom of the disease of the user (S134), acquire information on a drug taken by a patient or information on a statistical side effect probability, as illustrated in FIG. 6 of the drug and perform a comparison operation (S135). When the symptom of the disease of the user is the same as the side effect of the drug taken, the server device 200 may not reflect the relevant side effect experience in estimating the drug side effect probability of the user. Accordingly, the side effect probability may be prevented from being erroneously estimated, as the user misunderstands the symptom of the disease as the side effect produced from the drug taken.

When the symptom of the disease of the user is different from the side effect of the drug taken, the server device 200 may increase the side effect probability of the user for each ingredient of the drug taken (S136).

When the user takes a specific drug first and the side effect is not produced, the server device 200 acquires a statistical side effect probability as illustrated in FIG. 6 and sets the statistical side effect probability as the basic side effect probability of the user for the relevant drug. Then, the server device 200 may multiply the basic side effect probability by a preset incentive constant for reflecting the side effect experience of the user. The incentive constant may be greater than '1' which is experimentally determined.

For example, when the incentive constant is 1.5, the following description is made regarding that the first symptom and the second symptom are made after the user of FIG. 7A takes the drug including the 'A' ingredient and the 'B' ingredient first. The server device 200 may estimate the side effect probability of the first symptom of the user for the 'A' ingredient, as 15% (=10%×1.5), the side effect probability of the second symptom of the user for the 'A' ingredient, as 7.5% (=5%×1.5), and the side effect probability of the first symptom of the user for the 'B' ingredient, as 30% (=20%×1.5), The side effect probability of the second symptom may not be estimated, because the second symptom is not the statistical side effect of the 'B' ingredient.

Figure 7B:
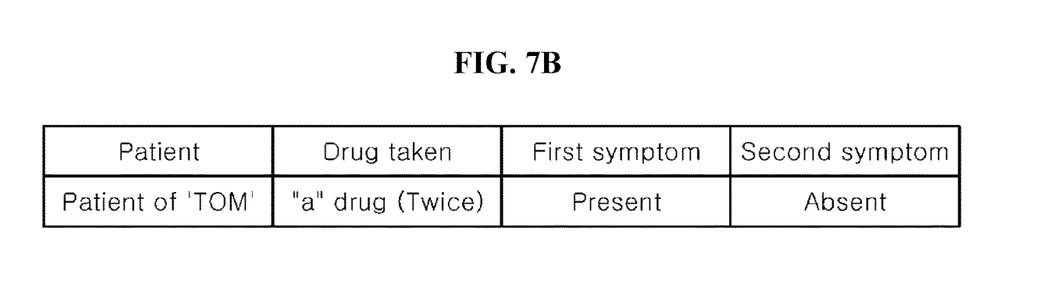

The following description will be made regarding a method for re-estimating (updating) the side effect probability of the drug, when the first symptom is made and the second symptom is not made as illustrated in FIG. 7B, after the user of FIG. 7A takes the drug including the 'A' ingredient and the 'B' ingredient again or takes a different drug including the 'A' ingredient and the 'B' ingredient.

When the incentive constant is 1.5 and when the disincentive constant is 0.5, the first symptom is made and the second symptom is not made after the user of FIG. 7B takes the drug including the 'A' ingredient and the 'B' ingredient, which has been taken previously. The server device 200 may update the drug side effect probability by applying the disincentive constant and the incentive constant to the side effect probabilities for the 'A' ingredient and the 'B' ingredient which are stored for the user.

For example, the server device 200 may estimate the side effect probability of the first symptom for the 'A' ingredient as 22.5% (=15%×1.5), the side effect probability of the second symptom for the 'A' ingredient as 3.75% (=7.5%×0.5), and the side effect probability of the first symptom for the 'B' ingredient as 45% (=30%×1.5), The side effect probability of the second symptom may not be estimated, because the second symptom is not the statistical side effect of the 'B' ingredient.

Figure 8A:
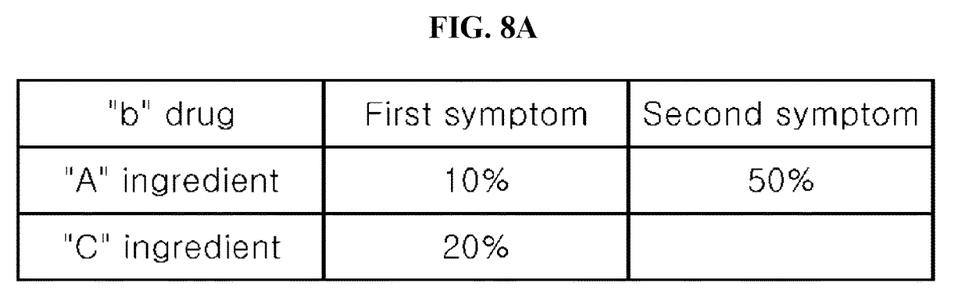
Figure 8B:
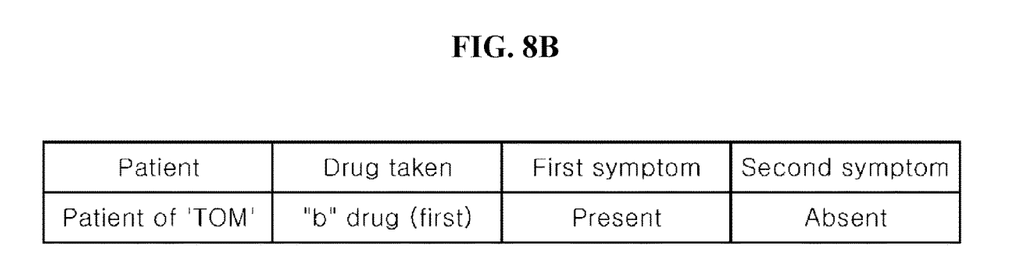

The following description will be made regarding the side effect probability after the user of FIG. 7B takes another drug including the 'A' ingredient. The following description will be made regarding a method for re-estimating (updating) the side effect probability of the drug, when the first symptom is made and the second symptom is not made as illustrated in FIG. 8B, after the user of FIG. 7B takes the drug 'b' including the 'A' ingredient and the 'C' ingredient again.

For a user 'TOM', currently, the personalized drug side effect probability may be updated to the side effect probability of 33.75% by applying the incentive constant of 1.5 to 22.5% which the personalized drug side effect probability for the first symptom of the 'A' ingredient, which is previously stored, and may be updated to the side effect probability of 1.875% by applying the disincentive constant of 0.5 to 3.75% which the personalized drug side effect probability for the second symptom of the 'A' ingredient which is previously stored. In addition, when the 'C' ingredient included in the drug 'b' is taken first, the personalized drug side effect probability for the 'C' ingredient may be estimated, as 15% by applying the incentive constant of 1.5 to the side effect probability of 10% for the first symptom of the 'C' ingredient.

According to another embodiment, when the statistical side effect probability value of the relevant drug or the gradient included in the relevant drug is absent from the data base, an initial value may be set as a specific constant value (significantly small value) in aspect of implementation.

The user may acquire the personalized drug side effect probability as the experience of the user of taking mutually different drugs redundantly containing some ingredients and may determine the drug to be avoided based on the acquired probability.

According to another embodiment, the server device 200 may set mutually different incentive constants for ingredients based on the statistical side effect of the drug or the ingredient contained in the ingredient.

For example, when the statistical side effect probability of the ingredient included in the drug is as illustrated in FIG. 6, the incentive constant for the first symptom of the 'A' ingredient may be set to be lower than the incentive constant for the first symptom of the 'B' ingredient. Accordingly, mutually different statistical probabilities may be reflected even with respect to a plurality of ingredients having the same side effect symptom such that the personalized drug side effect probability may be acquired.

According to another embodiment, the server device 200 may set mutually different incentive constants, based on the number of times of continuous experiences in which the same side effect is produced after the same ingredient is taken.

For example, the server device 200 may set an incentive constant when consecutively experiencing the first symptom of the 'A' ingredient twice, to be greater than the incentive constant when experiencing the first symptom of the 'A' ingredient. Accordingly, as the experience in which mutually different drugs are taken is accumulated, the personalized drug side effect probability may be more accurately acquired.

According to another embodiment, the server device 200 may set mutually different incentive constants, based on the strength of the side effect experienced by the user.

For example, the server device 200 may set an incentive constant when the user experiences the first symptom of the 'A' ingredient with the strength of '2' to be greater than an incentive constant when the user experiences the first symptom of the 'A' ingredient with the strength of '1'. The server device 200 may provide an interface, to the user terminal 100 to select the strength of a side effect experienced by the user. Accordingly, as the experience in which drugs are taken is accumulated, the personalized drug side effect probability may be more accurately acquired.

According to another embodiment, when the concentration of the drug, which is previously taken, in blood is equal to or greater than a specific level, that is, when the drug taken previously remains in the body, the server device 200 may exclude the experience of the drug previously taken from an experience for calculating the side effect probability of the drug.

For example, when the server device 200 identifies a time in which a user takes a drug including the 'A' ingredient, calculates the concentration of the 'A' ingredient in the blood based on the preset information on the body of the user, and exclude the experience of taking the drug including the 'A' ingredient from the experience for calculating the side effect probability of the drug, even if the side effect is produced when the concentration of the 'A' ingredient in the blood is equal to or greater than a preset reference. Accordingly, as the experience of the side effect is redundantly applied due to the previously taken drug, the side effect probability of the drug may be excluded.

The above-described disclosure is able to be implemented with computer-readable codes on a medium having a program. Computer-readable medium includes all types of recording devices having data which is readable by a computer system. For example, the computer-readable medium includes a hard disk drive (HDD), a solid state disk (SSD), a silicon disk drive (SDD), a ROM, a RAM, a CD-ROM, a magnetic tape, a floppy disk, or an optical data storage device. In addition, the computer may include the processor of the user terminal or the server device.

Meanwhile, the program is specially designed and configured for the inventive concept or may be known and available to those skilled in computer software. In addition, the program may include not only a machine code such as things generated by a compiler but also a high-level language code executable on a computer using an interpreter.

In the specification of this disclosure (especially, claims), the term 'the' and the use of a similar direction may correspond to both a singular form and a plural form. In addition, when this disclosure discloses a range, this disclosure includes an invention employing an individual value belonging to the range (unless otherwise specified), the individual value of the range is described in the detailed description.

Unless otherwise specified, steps constituting a method of this disclosure are performed in appropriate order. However, the disclosure is not limited to the described order of the steps. The use of all examples or exemplary terms (for example, 'or the like') in the disclosure is merely to describe the detailed description, and the disclosure is not limited thereto except for claims. In addition, those skilled in the art may form variations, modifications, combinations, and changes of claims within the scope of the claims depending on the design condition and the design factor.

Accordingly, the spirit of the inventive concept is not limited to the embodiment, and accompanying claims or equivalents thereof fall in the scope of the disclosure.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for estimating personalized probability of a drug side effect, the method comprising:
   recognizing, through a camera device of a user terminal, a product name of a drug taken by a subject, based on an image of a product package;
   identifying, by a server device, the drug based on the recognized product name;
   identifying, by the server device, an experience of a side effect, which is produced as the subject takes the drug, and input by the subject, based on data stored in a drug side effect database;
   estimating, by the server device, a probability of the side effect of the subject in relation to the drug, based on the experience of the side effect of the subject;
   transmitting, by the server device, the estimated probability of the side effect to the user terminal;
   receiving, by the user terminal, a user input of a particular drug;
   receiving, by the user terminal, a user input of a particular side effect, which is experienced by the subject;
   transmitting, by the user terminal, the user inputs to the server device;
   updating, by the server device, a side effect probability of the subject with respect to the drug taken by the subject or an ingredient contained in the drug;
   when the drug taken by the subject contains newly taken ingredients, and the side effect is produced, identifying, by the server device, a disease of the subject, and prescription information having a disease code of the subject, through an electronic medical record (EMR) server;
   identifying, by the server device, a symptom of the disease of the subject;
   acquiring, by the server device, information on the drug taken by the subject, or statistical information on the side effect probability of the drug taken by the subject;
   performing, by the server device, a comparison operation, in which, when the symptom of the disease of the subject is identical to the side effect of the drug taken, the server device does not reflect the experience of the side effect in estimating the probability of the side effect of the subject in relation to the drug, and when the symptom of the disease of the user is different from the side effect of the drug taken, the server device increases the side effect probability of the subject for each of the newly taken ingredients; and
   when the statistical information on the side effect probability of the drug is absent from the drug side effect database, setting, by the server device, an initial value as a specific constant value.

2. The method of claim 1, wherein the estimating of the probability of the side effect of the subject in relation to the drug includes:
   updating the probability of the side effect whenever the subject inputs an experience of taking the drug.

3. The method of claim 2, wherein the updating of the probability of the side effect includes:

updating the probability of the side effect, based on an experience, in which the side effect is not produced, input by the subject after the subject takes the drug.

4. The method of claim 2, wherein the updating of the probability of the side effect includes:

updating the probability of the side effect of the subject by applying mutually different algorithms depending on whether the side effect is produced after the subject takes the drug.

5. The method of claim 1, wherein the estimating of the probability of the side effect comprises:

calculating a concentration of the drug, which is previously taken, containing a first ingredient in blood, based on a time elapsed from a time in which the subject takes the drug containing the first ingredient previously, and information on a physical body of the subject, and estimating the probability of the side effect of the subject, based on the concentration of the drug in the blood.

6. A computing device comprising:

a processor; and a memory operatively connected to the processor to store at least one code executed by the processor, wherein the memory stores codes that when executed by the processor, cause the processor to:

identify a drug taken by a subject;

identify a side effect input from the subject, as the subject takes the drug; and estimate a probability of the side effect of the subject, in relation to the drug, based on an experience of the side effect of the subject transmit the estimated probability of the side effect to a user terminal;

update a side effect probability of the subject with respect to the drug taken by the subject or an ingredient contained in the drug;

when the drug taken by the subject contains newly taken ingredients, and the side effect is produced, identify a disease of the subject, and prescription information having a disease code of the subject, through an electronic medical record (EMR) server;

identify a symptom of the disease of the subject;

acquire information on the drug taken by the subject, or statistical information on the side effect probability of the drug taken by the subject;

perform a comparison operation, in which, when the symptom of the disease of the subject is identical to the side effect of the drug taken, the processor does not reflect the experience of the side effect in estimating the probability of the side effect of the subject in relation to the drug, and when the symptom of the disease of the user is different from the side effect of the drug taken, the processor increases the side effect probability of the subject for each of the newly taken ingredients; and when the statistical information on the side effect probability of the drug is absent from a drug side effect database, set an initial value as a specific constant value.

7. The computing device of claim 6, wherein the memory further stores a code that when executed by the processor, causes the processor to update the probability of the side effect, whenever the subject inputs the experience in which the subject takes the drug.

8. The computing device of claim 7, wherein the memory further stores a code that when executed by the processor, causes the processor to update the probability of the side effect of the subject, by applying mutually different algorithms depending on whether the side effect input is produced after the subject takes the drug.

* * * * *